US005482720A

United States Patent [19]
Murphy et al.

[11] Patent Number: 5,482,720
[45] Date of Patent: Jan. 9, 1996

[54] ENCAPSULATED CO-MICRONIZED BICARBONATE SALT COMPOSITIONS

[75] Inventors: Richard T. Murphy, Belle Mead; Wolfgang R. Bergmann, Princeton, both of N.J.

[73] Assignee: Church & Dwight Co., Inc., Princeton, N.J.

[21] Appl. No.: 320,864

[22] Filed: Oct. 11, 1994

[51] Int. Cl.⁶ .............................. A01N 59/00; A61K 9/14
[52] U.S. Cl. ..................... 424/489; 424/69; 424/401; 424/405; 424/409; 424/493; 424/641; 424/642; 424/717; 424/719; 424/722; 514/951; 514/770
[58] Field of Search ...................... 424/489, 493, 424/494, 497, 401, 69

[56] References Cited

U.S. PATENT DOCUMENTS 4,302,347 11/1981 Straw et al. ............................ 252/116
5,338,551 8/1994 Lajoie ..................................... 424/717
5,376,362 12/1994 Murphy et al. ........................... 424/66

Primary Examiner—Gollamudi S. Kishore
Assistant Examiner—James M. Spear
Attorney, Agent, or Firm—Charles B. Barris

[57] ABSTRACT

This invention provides an encapsulated co-micronized bicarbonate salt powder composition which is a blend of crystalline ingredients having a particle size between about 0.1–30 microns. The composition is produced by mill co-micronization of a crystalline bicarbonate ingredient and a crystalline inorganic compound ingredient having a Mohs hardness value between about 3–7, and then surface coating the particles with a polymer. A blend of crystalline particles such as sodium bicarbonate and zinc oxide is free-flowing and essentially free of agglomerated solids after co-micronization, and the discrete crystalline particles are coated with a polymer to form a present invention encapsulated co-micronized bicarbonate salt powder composition.

23 Claims, No Drawings

5,482,720

ENCAPSULATED CO-MICRONIZED BICARBONATE SALT COMPOSITIONS

CROSS-REFERENCE TO RELATED PATENT APPLICATION

The subject matter of this patent application is related to that described in patent application Ser. No. 08/219,873, filed Mar. 30, 1994, now U.S. Pat. No. 5,417,963.

BACKGROUND OF THE INVENTION

New commercial products are becoming available which provide special advantage because of fine particle size. Zinc oxide is widely utilized as an ingredient in human health products. Superior results are now obtained by the use of submicron transparent zinc oxide powder. The ultrafine zinc oxide provides advantage of UVA/B-protection in cosmetic formulations, and exhibits enhanced antimicrobial capacity and functions as a preservative.

Alkali metal bicarbonate is another commodity reagent which has found application in a broad variety of products such as laundry detergents, deodorizers, creams and lotions, dentifrices, antacids, buffers, fungicides, and the like.

There is evidence that fine particle size alkali metal bicarbonate or ammonium bicarbonate can exhibit increased reactivity in comparison with coarse grain bicarbonate salts. In soda cracker production, finely divided sodium bicarbonate ingredient is more efficiently distributed and effectively reactive during the cracker dough preparation. The finished baked cracker is an improved product which has a substantially uniform texture, flavor and surface color, and a consistent pH throughout.

The inclusion of particulate alkali metal bicarbonate in an antiperspirant-deodorant cosmetic stick provides a product with improved deodorant properties. However, coarse grain alkali metal bicarbonate has an undesirable tendency to settle in an antiperspirant-deodorant cosmetic stick matrix. The use of ultrafine alkali metal bicarbonate as a deodorant ingredient in cosmetic stick and roll-on type personal care products is being investigated, since the ultrafine particles have less tendency to settle than coarse grain particles when dispersed in a liquid or semi-solid matrix.

A limiting factor has been the unavailability of alkali metal bicarbonate or ammonium bicarbonate powder which is composed of free-flowing ultrafine particles that are not in an agglomerated state.

Dimensional instability of a cosmetic stick product containing bicarbonate ingredient, and the esthetic appearance and the "feel" on the skin, are additional difficulties encountered in the preparation of a low residue antiperspirant-deodorant cosmetic product. The high density of a suspended particle-phase of bicarbonate ingredient relative to the low density of an organic matrix phase contributes to the instability and settling of the bicarbonate particle phase in a cosmetic stick or roll-on personal care product.

In addition, a bicarbonate ingredient often is incompatible with the active astringent salts and with other ingredients of conventional cosmetic stick products. A bicarbonate ingredient in direct contact with acidic ingredients is susceptible to decomposition into carbon dioxide and water.

There is continuing interest in the development of reagents such as alkali metal bicarbonate and ammonium bicarbonate which have an ultrafine particle size, and exhibit a novel combination of properties when utilized as an ingredient in personal care, biologically active, household, and specialty type products. There is also interest in the development of a bicarbonate powder which is in a form that is stable when blended with an acidic ingredient in a formulation.

It is an object of this invention to provide an alkali metal bicarbonate or ammonium bicarbonate powder which has an ultrafine particle size, and which is free-flowing and essentially free of agglomerated solids.

It is a further object of this invention to provide a process for producing an ultrafine bicarbonate salt powder composition which is a co-micronized blend of crystalline compounds composed of discrete particles which are coated with a polymer.

Other objects and advantages of the present invention shall become apparent from the accompanying description and examples.

DESCRIPTION OF THE INVENTION

One or more objects of the present invention are accomplished by the provision of an encapsulated co-micronized bicarbonate salt powder composition comprising (1) discrete particles of at least one crystalline compound ingredient selected from alkali metal and ammonium bicarbonates, and (2) between about 10–50 weight percent of discrete particles of at least one crystalline inorganic compound ingredient having a Mohs hardness value between about 3–7; wherein the crystalline ingredients of the composition have an average particle size in the range between about 0.1–30 microns as obtained by mill co-micronization of the crystalline ingredients; and wherein the crystalline particles have a polymer surface coating.

In another embodiment this invention provides a process for producing an encapsulated co-micronized bicarbonate salt powder composition which comprises (1) blending ingredients comprising (a) at least one crystalline compound selected from alkali metal and ammonium bicarbonates, and (b) between about 10–50 weight percent of at least one crystalline inorganic compound having a Mohs hardness value between about 3–7; (2) milling the blend to co-micronize the ingredients to discrete particles having an average particle size in the range between about 0.1–30 microns; and (3) coating the particle surfaces with a polymer.

A blend of co-micronized crystalline particles is produced in step(2), and the particles characteristically are in an unagglomerated form, and the step(3) product is a blend of encapsulated ultrafine particles which has free-flow properties.

The bicarbonate salt starting material of an invention powder composition is selected from alkali metal and ammonium bicarbonates, such as sodium bicarbonate, potassium bicarbonate and ammonium bicarbonate, and mixtures thereof. The bicarbonate salt starting material can contain up to about 30 weight percent, based on the weight of bicarbonate ingredient, of an alkali metal or ammonium carbonate compound. The bicarbonate salt starting material before co-micronization typically has an average particle size in the range between about 40–600 microns.

The term "discrete" as employed herein refers to particles which are individually distinct solids.

The terms "average particle size" and "average diameter" as employed herein refers to the average of the largest dimension of particles.

The inorganic compound starting material is at least one compound having a Mohs hardness value between about 3–7. The inorganic compound ingredient is selected to have a Mohs hardness which is higher than the 2–3.5 Mohs hardness value of the alkali metal or ammonium bicarbonate ingredient.

Inorganic carbonates normally have an average Mohs value of about 3–4, inorganic silicates have an average Mohs value of about 5–6, and inorganic oxides have an average Mohs value of about 5–7.

Suitable inorganic compounds for purposes of the present invention compositions include calcium carbonate, copper carbonate, zinc carbonate, barium carbonate, magnesium carbonate, manganese carbonate, calcium silicate, magnesium silicate, copper silicate, manganese silicate, titanium dioxide, tin oxide, zinc oxide, silicon oxide, aluminum oxide, magnesium oxide, copper oxide, zirconium oxide, beryllium oxide, calcium fluoride, zinc sulfide, aluminum phosphate, and the like.

A blend of co-micronized crystalline particles obtained from step(2) of the invention process exhibits novel properties which are derived from the particular method of preparation, i.e., a crystalline bicarbonate salt compound is mill co-micronized with a crystalline inorganic compound having a Mohs hardness value between about 3–7.

If an alkali metal or ammonium bicarbonate salt as a sole ingredient is subjected to a mill micronization procedure, the resultant ultrafine powder tends to be in the form of cohesive agglomerated crystallites of primary particles, and the powder is not free-flowing.

The presence of a crystalline compound ingredient during a co-micronization procedure in step(2) of the invention process provides at least two advantages.

First, the crystalline inorganic compound ingredient serves as a grinding medium because of its particle hardness, and the average size of the bicarbonate salt particles is reduced into an ultrafine micron range.

Second, the presence of the ultrafine crystalline inorganic compound particles in a co-micronized powder composition inhibits agglomeration of the ultrafine bicarbonate salt particles, and the co-micronized powder is free-flowing.

In step(2) of the invention process, the co-micronized bicarbonate salt blend of ultrafine particles can be prepared by means of a grinding, impact or fluid energy type of milling equipment which is designed to micronize crystalline solids to ultrafine powders.

One type of mill involves the use of rollers or balls in combination with an annular grinding plate, such as bowl roll mills, roller mills and ring-ball mills. Another type of mill involves the use of a pulverizing rotor. These types of mills are illustrated in U.S. Pat. Nos. 2,253,839; 4,550,879; 4,562,972; 4,566,639; 4,919,341; and references cited therein.

Fluid energy jet mills have found application for the comminution of a wide variety of particulate solids. Jet mills are well adapted to micronize and particle size classify particulate solids into ultrafine powders. An important application is the micronization of pigments such as titanium dioxide.

Fluid energy jet mills are size reduction machines in which particles to be ground are accelerated in a stream of gas, (e.g., compressed air) and micronized in a grinding chamber by their impact against each other or against a stationary surface in the grinding chamber. Different types of fluid energy mills can be categorized by their particular mode of operation. Mills may be distinguished by the location of feed particles with respect to incoming air. In the commercially available Majac jet pulverizer (Majac Inc.), particles are mixed with the incoming gas before introduction into the grinding chamber. In the Majac mill, two streams of mixed particles and gas are directed against each other within the grinding chamber to cause fracture. An alternative to the Majac mill configuration is to accelerate within the grinding chamber particles that are introduced from another source, such as a mill with an annular grinding chamber into which numerous gas jets inject pressurized air tangentially (U.S. Pat. No. 3,565,348).

During jet mill grinding, particles that have reached the desired size are separated, while the remaining coarser particles continue to be ground. The particle size classification process can be accomplished by the circulation of the gas and particle mixture in the grinding chamber. In pancake type mills, the gas is introduced around the periphery of the cylindrical grinding chamber to induce a vorticular flow within the chamber. Coarser particles tend to the periphery where they are ground further, while finer particles migrate to the center of the chamber where they are drawn off into a collector outlet located in proximity to the grinding chamber.

Particle size classification can also be accomplished by a separate classifier. This type of classifier is mechanical and features a rotating vaned cylindrical rotor. The air flow from the grinding chamber only can force particles below a certain size through the rotor against the centrifugal forces imposed by the rotor's speed. These particles are the mill's micronized product. Oversized particles are returned to the grinding chamber.

Variation in fluid energy jet mill design are illustrated in U.S. Pat. Nos. 4,219,164; 4,261,521; 4,280,664; 4,526,324; 4,602,743; 4,638,953; 4,664,319; 4,811,907; 4,880,169; 4,962,893; 4,133,504; and references cited therein.

The application of the polymer coating to the blend of co-micronized particles in step(3) of the invention process is accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethylformamide, and the like, as appropriate for a selected polymer species. A coating polymer also can be applied in the form of an emulsion or suspension. After the coating medium is applied to the particles, the solvent medium is removed by evaporation, thereby forming a continuous film coating which encapsulates the discrete ultrafine particles.

The coating thickness on the particle surfaces typically will vary in the range between about 0.1–20 microns. The coating can consist of a single layer or multiple layers. The polymeric coating can constitute between about 5–50 weight percent of the total dry weight of the coated particles.

A polymer employed for coating the ultrafine particles in step(3) of the invention process is selected from hydrophilic organic polymers and hydrophobic (water-insoluble) organic polymers and mixtures thereof.

A hydrophilic polymer employed for coating the ingredient particles is selected from water-soluble and water-dispersible organic polymers. A mixture of polymers can be employed, and a content of between about 0.5–40 weight percent of a water-insoluble polymer, based on the coating weight, can be included with a hydrophilic polymer.

The term "hydrophilic" as employed herein refers to an organic polymer which has a water-solubility of at least about one gram per 100 grams of water at 25° C. The term "hydrophobic" or "water-insoluble" as employed herein refers to an organic polymer which has a water solubility of less than about one gram per 100 grams of water at 25° C.

Suitable hydrophilic polymers for coating co-micronized particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, polyacrylamide, and the like. Polyvinyl acetate is illustrative of a water-insoluble polymer which can be included as an additional coating component to moderate the hydrophilicity of a hydrophilic polymer coating.

Suitable water-insoluble polymers, alone or in combination with one or more other components, for coating co-micronized particles include polyvinyl acetate, polyacrylamide, polyvinyl chloride, polystyrene, polyethylene, polyurethane, and the like.

For purposes of release of the core matrix of crystalline bicarbonate salt or inorganic compound in the encapsulated particles when introduced into an aqueous environment, a surface coating of water-insoluble polymer preferably has a content between about 5–30 weight percent of a particulate water-extractable organic or inorganic filler, such as sodium bicarbonate, sodium carbonate, sodium chloride, calcium chloride, monosaccharide or disaccharide, sorbitol, mannitol, and the like.

The rate of release of bicarbonate salt or inorganic compound core matrix content of the particles under moisture conditions can be controlled by the quantity and type of polymer coating on the particle surfaces.

Low molecular weight hydrophilic polymers will release the particle core matrix content at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release the particle core matrix content at a relatively fast rate. Polyethylene oxide (M.W. of 4,000,000) or partially hydrolyzed polyvinyl acetate will release at a relatively slow rate. Polyvinylpyrrolidone will release the particle core matrix content at an immediate rate, when the encapsulated particles are in contact with an underarm type of moisture as an ingredient of a cosmetic stick or roll-on personal care product.

In another embodiment an encapsulated co-micronized bicarbonate salt powder composition of the present invention includes a content of anti-caking ingredient, in a sufficient quantity to provide and maintain free-flow properties in the powder composition over an extended period.

Suitable anti-caking agents include magnesium silicate, zinc silicate, calcium silicate, sodium aluminosilicate, silica aerogel, silica xerogel, bentonite, attapulgite clay, zinc stearate, magnesium palmitate, sodium phthalate, zinc sulfide, magnesium phosphate, zirconium oxychloride, and the like.

The present invention also contemplates the provision of a cosmetic powder such as a baby powder formulation. Illustrative of a novel baby powder product is a formulation which comprises a blend of (1) hydrophilic polymer-coated co-micronized sodium bicarbonate and zinc oxide particles as described hereinabove, and (2) between about 5–70 weight percent of cosmetic grade talc.

In a further embodiment this invention provides a powder composition which comprises a blend of (1) hydrophilic polymer-coated co-micronized bicarbonate salt and inorganic compound particles, and (2) between about 0.05–10 weight percent of a biocidal ingredient, such as 2,4,4'-trichloro-2'-hydroxydiphenyl ether (Triclosan).

A present invention encapsulated co-micronized bicarbonate salt powder composition exhibits a unique combination of properties because of the novel physical form of the free-flowing polymer-coated particles when utilized as an ingredient in personal care and specialty type products.

The inclusion of a present invention encapsulated co-micronized bicarbonate salt powder as an ingredient enhances odor absorption and neutralization in personal care products, such as those adapted for skin care, oral care or feminine hygiene usage.

A present invention encapsulated bicarbonate salt powder as an ingredient provides improved esthetics in creams, lotions, gels, ointments, soapbars, toothpastes, and the like. Irritation is minimized, skin mildness is improved, and antibacterial/antifungal activity is increased.

Another valuable property of a present invention co-micronized bicarbonate salt composition is an exceptional capability to blend readily into suspension formulations with other ingredients. The ultrafine size and polymer-coated surface area of the co-micronized particles facilitate the formation of a homogeneous solid-phase suspension in an organic medium which has long term stability.

Other advantages are achieved by the practice of the present invention. As noted in the Background section of the specification, the relative densities of liquid and solid phases in a cosmetic stick or roll-on personal care product directly affects the stability and esthetics of the formulations. Density matching of inorganic and organic phases is a significant factor in cosmetic stick and roll-on products. The present invention provides an encapsulated co-micronized bicarbonate salt deodorant ingredient of lower density which more closely matches the density of the organic matrix of a cosmetic stick or roll-on product than does uncoated bicarbonate ingredient.

When there is density matching of organic matrix and dispersed hydrophilic polymer-coated bicarbonate particle phases, a cosmetic stick or roll-on product has improved dimensional stability, and better esthetic appearance and "feel" when applied to human skin.

The following Examples are further illustrative of the present invention. The components and specific ingredients are presented as being typical and various modifications can be derived in view of the foregoing disclosure within the scope of the invention.

EXAMPLE I

This Example illustrates the preparation of a present invention co-micronized sodium bicarbonate/zinc oxide composition by air-jet milling.

Air-jet pulverized sodium bicarbonate is commercially available (Particle Size Technology, Inc.). The commercial sodium bicarbonate has an average particle size of about 5 microns, and 90 percent of the particles have a diameter less than 20 microns. The sodium bicarbonate is substantially in the form of crystallites of agglomerated primary particles which are not free-flowing.

In accordance with the present invention, air-jet milling equipment (similar to that in U.S. Pat. No. 4,880,169) is employed to prepare a free-flowing co-micronized composition consisting of 70 weight percent of sodium bicarbonate and 30 weight percent of zinc oxide. The co-micronized composition has an average particle size of about 20 microns. The co-micronized composition is unagglomerated and free-flowing.

The sodium bicarbonate starting material has an average particle size of about 50 microns. The zinc oxide starting material has an average particle size of about 10 microns, and a Mohs hardness value of about 4.

The procedure described above is repeated, except that magnesium oxide is substituted for the zinc oxide. The magnesium oxide has a Mohs hardness value of about 6. The sodium bicarbonate/magnesium oxide powder is substantially unagglomerated and free-flowing.

If sodium bicarbonate alone is jet-milled following the above-described procedure, an agglomerated product is obtained which is not free-flowing.

EXAMPLE II

This Example illustrates a fluidized bed procedure for coating a co-micronized mixture of bicarbonate salt and crystalline inorganic compound with a hydrophilic polymer in accordance with the present invention.

A fluidized bed vessel is utilized which is equipped with a Wurster air-suspension coater system (WARF) as described in U.S. Pat. No. 4,568,559 and 4,877,621.

A coating solution is prepared by dissolving polyethylene glycol (45 g, Poly-G 2000, Olin Corp.), and propylene glycol butyl ether (10 g, PPG 14, Americol) in ethanol (500 g)/water (75 g).

A co-micronized powder of sodium bicarbonate and zinc oxide prepared by the method illustrated in Example I is utilized as the core matrix discrete particles. The co-micronized powder is charged into the coating chamber of the coater system.

Compressed air is introduced into the coating chamber, and the polymeric coating solution is sprayed on the air-suspended co-micronized core matrix particles, until the coating weight is about 30% of the total dry weight of the coated particles.

The procedure is repeated, except that Hydroxypropylmethylcellulose (Methocel 60 HG, Dow Chemical Co.) is employed as the hydrophilic polymer.

The procedure is repeated, except that multodextrin (Lodex 10; Durkee Foods) or amylodextrin is employed as the water-soluble polymer, and 0.5 g of a surfactant is included in the solution (polyoxyethylenesorbitan monolaurate; Tween 20; ICI Americas, Inc.).

The procedure is repeated except that a co-micronized mixture of discrete potassium bicarbonate and calcium fluoride particles are employed as the encapsulated core matrix.

The above described procedures produce encapsulated co-micronized bicarbonate salt powder compositions which have an average particle size between about 22–35 microns.

EXAMPLE III

This Example illustrates a procedure for the preparation of an antiperspirant-deodorant cosmetic stick product in accordance with the present invention.

A stainless steel tank is provided which is equipped with turbine agitation.

Silicone oil DC 245 (400 lbs, Dow Corning) and Dow DC 200 (37.50 lbs, Dow Corning) are charged to the mixing tank. Agitation (55–65 RPM) is initiated, and heating the liquid medium to 176° F. is commenced.

During the heating period, the following ingredients are added to the stirred liquid medium:

|  | lbs. |
|---|---|
| Lanette 18 DEO[1] | 175.00 |
| Castorwax MP-80[2] | 31.25 |
| ICI G-2162[3] | 6.25 |

[1]Stearyl alcohol; Henkel.
[2]Hydrogenated castor oil; RTD.
[3]PEG 25 PG stearate; ICI.

The mixture is stirred at 176° F. for about 30 minutes until the ingredients are melted and the liquid medium is homogeneous. The stirring speed is reduced to about 35 RPM, then Cyprus Supra A Talc 1625 (18.75 lbs, Cyprus) and Reach AZP 908 aluminum-zirconium tetrachlorohydrex glycine (312.50 lbs, Reheis) are added. The temperature is maintained at 176° F. for about 40 minutes until the fluid medium is uniform, and then the temperature is lowered to 154° F.

Encapsulated co-micronized sodium bicarbonate/zinc oxide (70/30; 140 lbs.) and Sobica F41 fragrance (6.25 lbs, Takasago) respectively are added with stirring to Silicone oil DC 245 (200 lbs, Dow Corning) in a second mixing tank at a temperature of 154° F. to form a homogeneous suspension medium. The sodium bicarbonate/zinc oxide particles are pre-coated with amylodextrin following the procedure described in Example II. The encapsulated particles have an average particle size of about 30 microns.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is (ASTM Method D5).

A second deodorant cosmetic stick product is prepared by eliminating the antiperspirant ingredient, and increasing the quantity of co-micronized sodium bicarbonate/zinc oxide ingredient from 140 lbs to 250 lbs in the above described manufacturing process.

EXAMPLE IV

This Example illustrates the preparation of an antiperspirant-deodorant roll-on product in accordance with the present invention.

A roll-on formulation is prepared by blending the following proportions of ingredients:

|  | lbs. |
|---|---|
| Silicone oil DC 245 | 60.90 |
| Quaternium-18 hectorite clay (Rheox) | 10.00 |
| Reach AZP 908 | 23.00 |
| Encapsulated potassium bicarbonate/zinc oxide | 5.00 |

|  | lbs. |
|---|---|
| (80/20)[(1)] | |
| Cab-o-Sil fumed silica (Cabot) | 0.60 |
| Sobica | 0.50 |

[(1)]Discrete particles are pre-coated with amylodextrin following the procedure described in Example II. The encapsulated particles have an average particle size of about 26 microns.

The roll-on formulation exhibits excellent dimensional stability when packaged and maintained under storage conditions for six months.

What is claimed is:

1. An encapsulated co-micronized bicarbonate salt powder composition comprising (1) discrete particles of at least one crystalline compound ingredient selected from alkali metal and ammonium bicarbonates, and (2) between about 10–50 weight percent of discrete particles of at least one crystalline inorganic compound ingredient having a Mohs hardness value between about 3–7; wherein the crystalline ingredients of the composition have an average particle size in the range between about 0.1–30 microns as obtained by mill co-micronization of the crystalline ingredients; and wherein the crystalline particles have a polymer surface coating.

2. A powder composition in accordance with claim 1 wherein the encapsulated bicarbonate particles are selected from the group consisting of sodium bicarbonate, potassium bicarbonate and ammonium bicarbonate.

3. A powder composition in accordance with claim 1 wherein the encapsulated inorganic compound particles are selected from the group consisting of metal oxide, metal carbonate, metal phosphate and metal sulfide.

4. A powder composition in accordance with claim 1 wherein the encapsulated inorganic compound particles are zinc oxide.

5. A powder composition in accordance with claim 1 wherein the co-micronization is by fluid energy milling.

6. A powder composition in accordance with claim 1 wherein the co-micronization is by grinding or impact milling.

7. A powder composition in accordance with claim 1 wherein the polymer surface coating on the particles comprises between about 5–50 weight percent of the dry particle weight.

8. A powder composition in accordance with claim 1 wherein the surface coating on the particles is a hydrophilic polymer or a water-insoluble polymer or a mixture thereof.

9. A powder composition in accordance with claim 1 wherein the surface coating on the particles is a polysaccharide coating.

10. A powder composition in accordance with claim 1 wherein the surface coating on the particles is a hydrocolloid.

11. A powder composition in accordance with claim 1 wherein the surface coating on the particles is a starch coating.

12. A powder composition in accordance with claim 1 wherein the surface coating on the particles is maltodextrin or amylodextrin or a mixture thereof.

13. A powder composition in accordance with claim 1 wherein the surface coating on the particles is a hydrophilic polymer having a content between about 0.5–40 weight percent of a water-insoluble polymer, based on the coating weight.

14. A powder composition in accordance with claim 1 wherein the surface coating on the particles is a water-insoluble polymer having a content between about 5–30 weight percent of a particulate water-soluble organic or inorganic filler.

15. A powder composition in accordance with claim 1 which has a content between about 1–20 weight percent of particulate anti-caking ingredient and is free-flowing.

16. A powder composition in accordance with claim 1 which has a content between about 5–70 weight percent of talc, and the composition is a cosmetic powder formulation.

17. A powder composition in accordance with claim 1 which has a content between about 0.05–10 weight percent of biocidal ingredient.

18. A process for producing an encapsulated co-micronized bicarbonate salt powder composition which comprises (1) blending ingredients comprising (a) at least one crystalline compound selected from alkali metal and ammonium bicarbonates, and (b) between about 10–50 weight percent of at least one crystalline inorganic compound having a Mohs hardness value between about 3–7; (2) milling the blend to co-micronize the ingredients to discrete particles having an average particle size in the range between about 0.1–30 microns; and (3) coating the particle surfaces with a polymer.

19. A process in accordance with claim 18 wherein the ingredients comprise sodium bicarbonate and zinc oxide.

20. A process in accordance with claim 18 wherein the co-micronization step is by air-jet milling.

21. A process in accordance with claim 18 wherein the co-micronization step is by grinding or impact milling.

22. A process in accordance with claim 18 wherein the particle surface coating is a hydrophilic polymer or a water-insoluble polymer or a mixture thereof.

23. A process in accordance with claim 18 wherein the particles in step (3) are contacted with a solvent solution of polymer, and the solvent is removed to form a continuous film surface coating which encapsulates the discrete particles.

* * * * *